United States Patent [19]
Barnicki et al.

[11] Patent Number: 5,660,691
[45] Date of Patent: *Aug. 26, 1997

[54] PROCESS FOR THE PRODUCTION OF TOCOTRIENOL/TOCOPHEROL BLEND CONCENTRATES

[75] Inventors: Scott Donald Barnicki; Charles Edwan Sumner, Jr.; Hampton Loyd Chip Williams, III, all of Kingsport, Tenn.

[73] Assignee: Eastman Chemical Company, Kingsport, Tenn.

[*] Notice: The term of this patent shall not extend beyond the expiration date of Pat. No. 5,512,691.

[21] Appl. No.: 558,073

[22] Filed: Nov. 13, 1995

[51] Int. Cl.$^6$ ................................................. C07D 311/76
[52] U.S. Cl. ........................... 203/72; 203/28; 203/80; 549/413
[58] Field of Search .................... 203/28, 29, 72, 203/80; 549/413

[56] References Cited

U.S. PATENT DOCUMENTS

| | | |
|---|---|---|
| 2,432,181 | 12/1947 | Trent . |
| 3,153,055 | 10/1964 | Brown et al. . |
| 3,335,154 | 8/1967 | Smith . |
| 4,454,329 | 6/1984 | Takagi et al. . |
| 4,977,282 | 12/1990 | Baldwin et al. ............. 549/413 |
| 5,371,245 | 12/1994 | Rindone et al. ............. 549/413 |
| 5,424,457 | 6/1995 | Summer, Jr. et al. ............. 549/413 |
| 5,487,817 | 1/1996 | Fizet ............................... 203/38 |
| 5,512,691 | 4/1996 | Barnicki et al. ............. 549/413 |

OTHER PUBLICATIONS

Lipids Handbook, 2d Ed., (1994) Chapman & Hall, p. 129.
T. Gordon, et al., "High Density Lipoproteins as a Protective Factor Against Coronary Heart Disease", The American Journal of Medicine, 62, pp. 707–714 (1977).

*Primary Examiner*—Timothy McMahon
*Attorney, Agent, or Firm*—Bernard J. Graves; Rose M. Allen; Harry J. Gwinnell

[57] ABSTRACT

Disclosed is an improved process for the preparation of tocotrienol/tocopherol blend concentrates from vegetable oil distillates which are enriched in tocotrienols. Tocotrienol/tocopherol blend concentrates are obtained containing 20–80% tocotrienols/tocopherols by weight, with an overall recovery of tocotrienols/tocopherols of 72% to 97%. The process is comprised first of an esterification reaction where the more volatile alcohols are converted to their less volatile fatty acid esters, followed by a series of distillation steps where components boiling higher and lower than the tocotrienols/tocopherols are separated from tocotrienols/tocopherols and other like boiling substances. Advantages of the process are that tocotrienol/tocopherol blend concentrates are produced efficiently and economically in a minimum number of steps without the use of solvents and with a relatively small capital investment.

49 Claims, 2 Drawing Sheets

PROCESS FOR THE PRODUCTION OF TOCOTRIENOL/TOCOPHEROL BLEND CONCENTRATES

FIELD OF THE INVENTION

This invention belongs to the field of organic chemistry. In particular, this invention relates to a process for the manufacture of tocotrienol/tocopherol concentrates from the by-products of vegetable oil refining.

BACKGROUND OF THE INVENTION

Alpha, beta, gamma, and delta tocopherol (hereafter referred to as tocopherols) can be found in various ratios and concentrations in crude vegetable oils such as soy bean, sunflower, canola, rapeseed, cottonseed, safflower, corn, palm, palm kernel, and rice bran oil. Palm oil and rice bran oil in particular contain high levels of both tocopherols and tocotrienols, whereas other vegetable oils contain primarily tocopherols. Typical crude palm oils contain 600–700 mg/Kg tocopherols and tocotrienols (50% tocotrienols) and crude rice bran oil contains 800–900 mg/Kg tocopherols and tocotrienols (57% tocotrienols). (See, for example, *Proc. Malays. Biochem. Soc. Conf.* (1983). pp. 15–17 and *Lipids Handbook*, 2d Ed., (1994) Chapman & Hall, p. 129.) Tocopherols and tocotrienols are a valuable constituent of vegetable oil as they help prevent oxidation and spoilage. Tocotrienols are of special interest for their hypocholesterolemic effects, as they decrease the blood level of the low density lipoprotein fraction of cholesterol and the total serum cholesterol, while increasing the ratio of the high density lipoprotein fraction of cholesterol to the low density lipoprotein fraction. Such effects have been shown to be clinically significant in lowering the risk of heart disease. (T. Gordon, et al., "High Density Lipoproteins as a Protective Factor Against Coronary Heart Disease", *The American Journal of Medicine*, 62, pp. 707–714 (1977)). During the refining of vegetable oils a large fraction of the tocopherols are lost to various by-products and waste streams. These waste and by-products streams include, but are not limited to, deodorizer distillates, steam refining distillates, and acidulated soapstocks. The vegetable oil refining by-products typically contain from less than 1% to greater than 20% tocopherol by weight. Such by-products from the tocotrienol-enriched vegetable oils such as rice bran oil and palm oil generally contain about 0.1 to 5% by weight of tocotrienols. The oil refining by-products are a valuable source of raw material for the production of natural vitamin E and other tocopherol antioxidants. However, the by-product streams also contain 20 to 99% by weight free fatty acids, less than 1% to 20% by weight sterols, less than 1% to 20% by weight sterol esters of fatty acid, less than 1% to 40% by weight mono, di, and triglycerides, less than 1% to 30% by weight hydrocarbons, and several percentage by weight of other compounds, in addition to tocopherols and tocotrienols. Thus, in order to obtain a tocopherol/tocotrienol concentrate stream useful for production of high purity vitamin E, it is necessary to remove these substances.

Numerous methods have been proposed for the recovery of tocopherols from vegetable oil refining by-products. For example, U.S. Pat. No. 2,432,181 teaches that tocopherols can be recovered from vegetable oils and fats by reacting the fatty acid glycerides with an aliphatic monohydric alcohol in the presence of an alkaline alcoholysis catalyst, followed by a flash distillation of residual alcohol glycerol, and fatty acid esters.

U.S. Pat. No. 3,153,055 teaches a process for the isolation of sterols and tocopherols from deodorizer distillate by esterification of free fatty acids and glycerides into lower monohydric alcohol esters under strongly acidic conditions. The sterols and tocopherols are fractionally extracted from the esterification product with a combination of polar and nonpolar solvents.

U.S. Pat. No. 3,335,154 teaches that deodorizer distillate can be saponified and acidulated to convert glycerides and sterol esters to free fatty acids and free alcohols (glycerol, sterols respectively). The free fatty acids are esterified with a monohydric lower alcohol and mineral acid catalyst. The sterols are precipitated/crystallized by the addition of water to the mixture, and the tocopherols are concentrated by removal of the fatty acid esters by molecular distillation.

All of the above processes suffer from serious drawbacks. They require the addition of extraneous monohydric alcohols and result in the production of fatty acid esters which are not normally present in the vegetable oil by-product feed material. The excess monohydric alcohol must be removed in an additional processing step. In order to produce a highly concentrated tocopherol product the sterols must either be removed by crystallization or by other means. Saponification requires large amounts of caustic and acid for acidulation, thereby creating excessive salt wastes.

U.S. Patent No. 4,454,329 teaches that a tocopherol concentrate can be obtained from deodorizer distillates by esterification of the free fatty acids with a dihydric or polyhydric alcohol, in the presence or absence of an acid catalyst. The esterification is preferably carried out in the presence of an aromatic solvent such as benzene, toluene, or xylene. The esterified mixture is then subjected to either a solvent extraction or a molecular distillation to produce the final tocopherol concentrate. Preferably, the solvent extraction is proceeded by a hydrogenation to convert the unsaturated triglycerides into saturated triglycerides, thereby decreasing the solubility of the triglycerides in the solvent phase of the extraction. Distillation of the esterified mixture concentrates tocopherols, sterols, hydrocarbons and other components with similar boiling points in the distillate. The triglycerides and other high-boiling components are left in the distillation residue.

The above process is unsatisfactory for a number of reasons. Deodorizer distillates and the like typically contain a 1/1 to 3/1 ratio of sterols to tocopherols, depending on the vegetable oil source. The tocopherols and sterols have very similar boiling points and therefore cannot be separated by distillation alone. The esterification is not run in such a fashion to ensure that the sterols are converted into sterol esters (which have a much higher boiling point than tocopherol). The distillate containing the tocopherols and sterols produced by the above process must be further treated by other separation techniques in order to produce a tocopherol concentrate essentially free of sterols.

In the solvent extraction version of the process, the solvent must be removed from the tocopherol extract, adding additional cost and complication to the process. The preferred embodiment of the solvent extraction, proceeded by the hydrogenation, adds still another step, with concomitant cost and complication. In addition, typical copper and nickel hydrogenation catalysts are known to be prooxidants, which promote the destruction of tocopherol, thereby lowering the yield of tocopherol from the process.

BRIEF DESCRIPTION OF THE DRAWINGS

FIGS. 1 and 2 are more fully described below.

SUMMARY OF THE INVENTION

Figure 1:
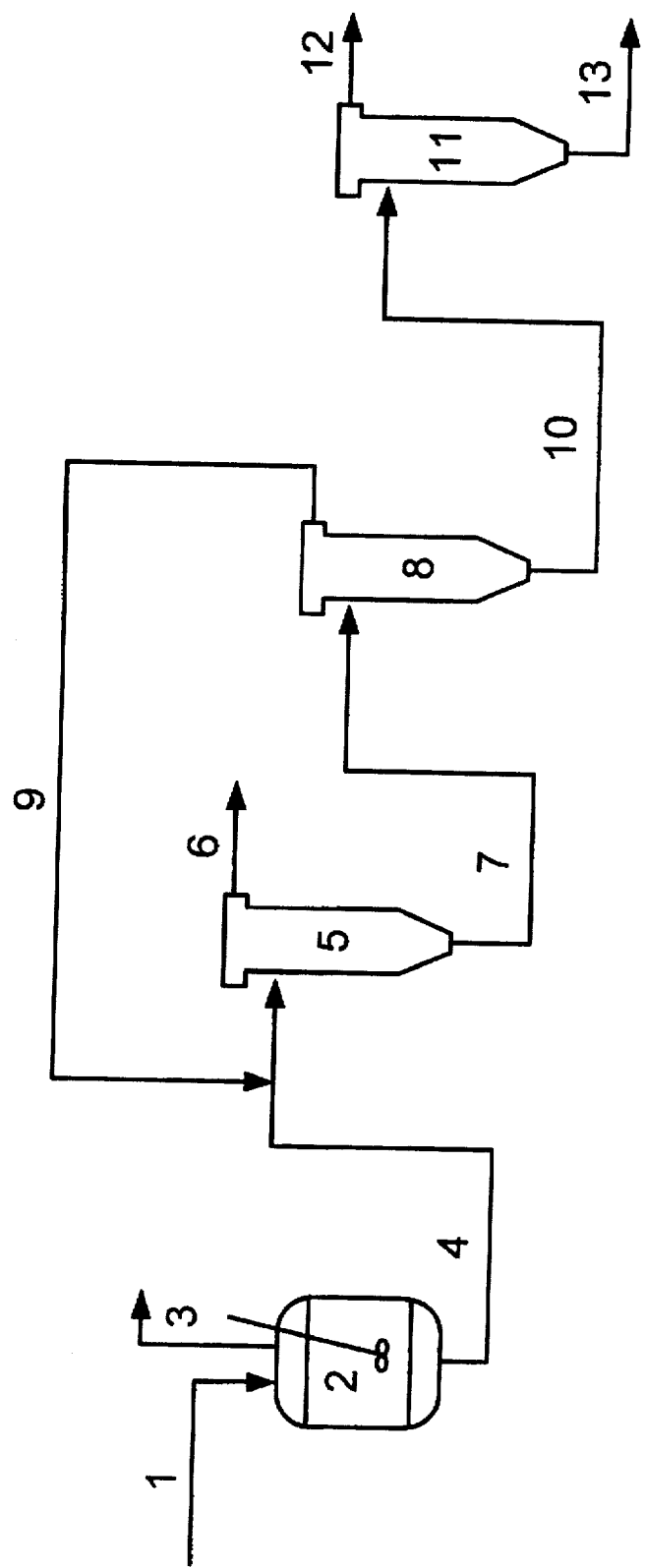
FIG. 1 is a diagram outlining one aspect of the method of the present invention, in which an esterification reaction is conducted in reactor (2), which is then subjected to a series of distillation steps (5), (8), and (9), to provide the desired tocopherol.

One object of this invention is to provide an efficient, economical process for the isolation of tocopherol/tocotrienol blend concentrates. This invention is directed to the isolation of such blend concentrates from vegetable oil by-products from sources which have relatively high amounts of tocotrienols as well as tocopherols. Such sources include rice bran oil and palm oil. Typically such sources will have approximately 0.1 to 5 weight percent of tocotrienols and 0.1 to 5 weight percent of tocopherols. Since the tocopherols and tocotrienols have very similar physical properties, they will be isolated in the method of the present invention as a blend. The raw material for the process can be deodorizer distillate, steam refining distillate, acidulated soapstock, or any other vegetable oil by-product from these tocotrienol rich vegetable oils.

In this invention, the vegetable oil by-product is subjected to an esterification step, with or without an acid catalyst, in which the sterols react with the free fatty acid already present in the mixture to form high-boiling sterol esters. Any other alcoholic moieties, triterpenoid alcohols, methyl-sterols, and the like, are converted to high-boiling fatty acid esters and waxes. Moreover, any mono- and di- fatty acid glycerides are largely converted to triglycerides by reaction with the free fatty acids. The tocopherols/tocotrienols also react to a limited extent; the extent of reaction can be controlled by proper selection of reaction time and temperature. The esterified mixture is then subjected to a series of distillation steps in which components boiling higher and lower than the tocopherols/tocotrienols are separated from tocopherols/tocotrienols and other like-boiling substances. The distillation steps consist of one or more separate distillation operations to remove unreacted free fatty acids overhead, along with any low-boiling compounds, from a tocopherol/tocotrienol-rich bottoms product and one distillation operation to remove a tocopherol/tocotrienol-rich product overhead from sterol esters, fatty acid polyesters of glycerol, waxes, and other high-boiling substances. Either the distillation operations to remove the fatty acid and low-boilers, or the distillation operation to remove the high-boilers may be done first. The resulting product of the process is a tocotrienol/tocopherol concentrate comprised primarily of tocopherols, tocotrienols, and hydrocarbons with similar boiling points, which is essentially free of free fatty acids, sterols, sterol esters, fatty acid polyesters of glycerol, waxes, and other high-boiling compounds.

As a further aspect of this invention, the catalyst for the esterification step is a monoalkyl tin compound, zinc salt of an organic acid, titanium (IV) alkoxides, zinc oxide, phosphoric acid or other mild mineral acids.

DETAILED DESCRIPTION OF THE INVENTION

The present invention provides a method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1, by weight, based on the concentration of tocopherols, optionally in the presence of an acid catalyst, said by-product optionally containing additional $C_{10}-C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides; and (b) followed by subjecting said mixture to a series of distillation operations comprising:

(i) one or more separate distillation operations, wherein said distillation(s) is (are) conducted at a temperature of about 200° C. to 320° C. and a pressure of about 0.01 torr to 10 torr, in series wherein unreacted fatty acids and low-boiling components are removed as a vapor effluent and a liquid effluent comprised of tocopherols and tocotrienols is removed; and (ii) wherein said liquid effluent from step (b)(i) is subjected to one or more distillations in series, wherein said distillation(s) is (are) conducted at a temperature of about 170° C. to 270° C. and a pressure of about 0.005 torr to 2 torr, wherein a tocotrienol/tocopherol concentrate is removed as a vapor effluent and wherein a liquid effluent comprised of sterol esters, fatty acid esters, glycerides, waxes, and other high-boiling substances is removed.

Figure 2:
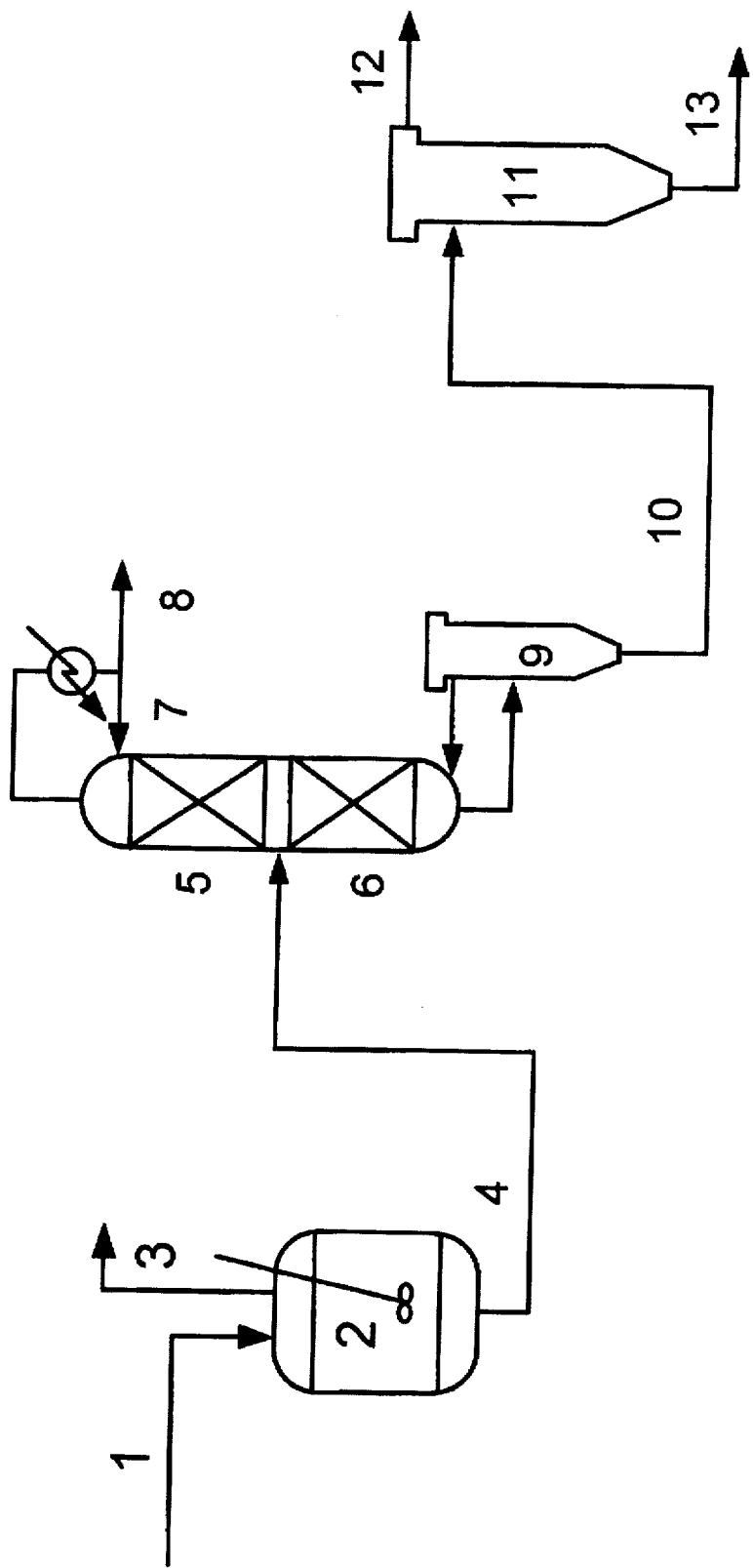
FIG. 2 is a diagram outlining the preferred method of the present invention, in which an esterification reaction is conducted in reactor (2), and subjected to two distillation steps.

The description of a preferred aspect of the present invention is made in reference to the process diagrams of FIGS. 1 and 2. The tocotrienol-rich vegetable oil by-product is fed via line (1) to a stirred tank or batch reactor, unit (2), operating at a temperature of about 70°–300° C., preferably in the range of 150°–230° C., and at a pressure of about 50 torr to 760 torr, preferably about 100–200 torr. The residence time in the reactor is preferably from about 1 to 24 hours, most preferably 90 minutes to two hours in the presence of an acid catalyst, and from two hours to ten hours when no catalyst is used. Preferred catalysts include monoalkyl tin compounds, zinc salt of an organic acid, titanium (IV) alkoxides, zinc oxide, phosphoric acid and other mild mineral acids.

During the reaction step, the free fatty acid which is already present in the feed mixture reacts with the sterols to form high-boiling sterol esters and water. Any other alcoholic moieties, triterpenoid alcohols, methyl-sterols, and the like, also react with the free fatty acids to form high-boiling fatty acid esters, waxes, and water. Moreover, any mono- and di- fatty acid esters of glycerol are largely converted to triglycerides by esterification with the free fatty acids. The tocopherols and tocotrienols also react to a limited extent with the free fatty acid to form tocopherol and tocotrienol esters and water. The relative rates of the esterification reactions is glycerides>sterols>tocopherols/tocotrienols. Thus, the reaction of tocopherols/tocotrienols can be controlled by proper selection of reaction temperature and time. Tocopherol/tocotrienol recovery from the reaction step is typically 80% to 97%, more typically 85% to 92%. Conversion of sterols to fatty acid sterol esters is typically 75% to 100%, more typically 85% to 95%. In a preferred embodiment, $C_{10}-C_{22}$ fatty acids are added to the starting material by-product, most preferably in an amount of up to about 40% by weight, based on the total weight of the by-product starting material.

The reactor is provided with a means for removal of the water of esterification, line (3). The removal of the water of esterification drives the reaction equilibrium toward the formation of the fatty acid ester products.

The esterification product (4) is then subjected to a series of distillation steps in which components boiling higher and lower than the tocopherols and tocotrienols are separated from tocotrienols/tocopherols and other like-boiling substrates. The distillation steps are one or more separate distillation operations to remove unreacted free fatty acids overhead along with any low-boiling compounds from a tocotrienol/tocopherol-rich bottoms product, and one distillation operation to remove a tocotrienol/tocopherol-rich product overhead away from sterol esters, fatty acid polyesters of glycerol, waxes, and other high-boiling compounds. Either the distillation operations to remove the fatty acid and low-boilers, or the distillation operation to remove the high-boilers may be done first. It should be understood that the reaction and distillation operations may be accomplished in batch, semi-batch, and continuous modes of operation.

This process produces tocotrienol/tocopherol blend concentrates efficiently and economically in a minimum of steps. No extraneous substances are added to the raw material oil, except possibly an esterification catalyst and added $C_{10}$–$C_{22}$ fatty acids. No solvents or excess esterification alcohols need to be removed from the reaction product. The achievable tocotrienol/tocopherol concentration in the final product is in the range of 20–80% tocotrienol/tocopherol by weight, depending on the amount of hydrocarbons in the starting material. More typically the product will have a tocotrienol/tocopherol concentration of 30–60% by weight of tocotrienol/tocopherol. The overall recovery of tocotrienol/tocopherol blend from the process is typically 72% to 97%, more typically 75% to 92%, most typically 80% to 85%.

One embodiment of the method of the present invention is illustrated by FIG. 1. The product (4) from the esterification step is distilled in unit (5) under high vacuum to remove a substantial fraction, typically 50–90%, more typically 60–80%, of the unreacted fatty acid along with a substantial fraction the low-boilers, stream (6), to leave a tocotrienol/tocopherol-rich bottoms product (7). The distillation operation is conducted at temperatures and pressures such that the tocotrienol/tocopherol are largely left in the bottoms product. The temperature and pressure of distillation operation (5) is in the range of 170° C. to 270° C., 0.05 to 10 torr. The preferred range is 200° C. to 240° C., 0.5 torr to 4 torr. The distillation apparatus (5) (as are all of the distillation equipment used herein) is preferably a high-vacuum design including a short path evaporator, a wiped-film evaporator, a centrifugal molecular still, or a falling film evaporator capable of low pressure operation.

The bottoms product (7) of the first distillation operation (5) is distilled a second time in distillation operation (8) under high vacuum to remove any remaining unreacted fatty acids and other low-boiling compounds. The temperature of distillation (8) must be higher or the pressure lower than distillation (5) in order to ensure essentially complete removal of any remaining fatty acids. The temperature and pressure of distillation (8) is in the range of 230° C. to 300° C., 0.01 to 5 torr. The preferred range is 240° C. to 280° C., 0.1 torr to 2 torr. Under these conditions a portion, typically 5–30%, of the tocotrienols/tocopherols will distill overhead with the remaining fatty acids into stream (9), leaving an acid-free tocotrienol/tocopherol-rich bottoms product (10). The distillate (9) containing some tocotrienols/tocopherols and the remaining free fatty acid may be discarded or recycled to reactor (2) or the first distillation operation (5) in order to improve the overall yield of tocotrienols/tocopherols. Since distillation (5) and distillation (8) are conducted under different temperature and pressure conditions, they act in combination as a multi-equilibrium staged device, lowering tocotrienol/tocopherol losses and increasing fatty acid removal. The distillation apparatus (8) may be of any high-vacuum design including a short path evaporator, wiped-film evaporator, centrifugal molecular still, or falling film evaporator.

The tocotrienol/tocopherol-rich bottoms product (10) of the second distillation (8) is then subjected to a third high-vacuum distillation (11). The tocotrienol/tocopherol and other similarly boiling compounds are collected as a final tocotrienol/tocopherol-rich distillate product (12). The triglycerides, sterol esters, other high-boiling fatty acid esters, and other high-boiling compounds are removed in the largely tocotrienol/tocopherol-free bottoms (13) of the distillation. Tocotrienol/tocopherol recovery to stream (12) is typically 95% to 100%, more typically 96% to 99.9%. The catalyst, if any were used, exits in the residue. The temperature and pressure of distillation operation (11) is in the range of 170° C. to 270° C., 0.005 to 2 torr. The preferred range is 200° C. to 250° C., 0.01 torr to 0.05 torr. The distillation apparatus (11) may be of any high-vacuum design including a short path evaporator, wiped-film evaporator, centrifugal molecular still, or falling film evaporator.

Thus, as a further aspect of the present invention, there is provided a method for preparing a tocotrienol/tocopherol blend concentrate which comprises the steps:

(a) heating a vegetable oil by-product comprised of tocopherols, tocotrienols, fatty acids, sterols, sterol esters of fatty acids, and mono-, di-, and triglycerides, wherein said tocotrienols are present in a proportion of about 0.5:1 to 10:1 based on the concentration of tocopherols, said by-product optionally containing added $C_{10}$–$C_{22}$ fatty acids, optionally in the presence of an acid catalyst, at a temperature of about 70° to 300° C. and a pressure of about 50 torr to 760 torr, while continuously removing water formed thereby, to form a mixture comprised of sterol esters, high boiling fatty acid esters, waxes, and glycerides;

(b) followed by subjecting said mixture to distillation at a temperature of about 170° C. to 270° C. and a pressure of about 0.05 to 10 torr, while removing unreacted fatty acids and low-boiling components as a vapor effluent and a liquid effluent comprised of tocopherols and tocotrienols;

(c) followed by subjecting the liquid effluent from step (b) to distillation at a temperature of about 230° C. to 300° C. and a pressure of about 0.01 to 5 torr, while removing remaining fatty acids and approximately 5 to 30 percent of total tocopherols as a vapor effluent and a liquid effluent which is a tocotrienol/tocopherol-enriched product; and (d) followed by subjecting the liquid effluent from step (c) to distillation at a temperature of about 170° C. to 270° C. and a pressure of about 0.005 to 2 torr, and collection and isolation of a tocotrienol/tocopherol blend concentrate as a vapor effluent.

As noted above, preferred apparatus for the distillation steps include any high-vacuum design including a short path evaporator, wiped-film evaporator, centrifugal molecular still, or falling film evaporator. Accordingly, as a further aspect of the present invention, there is provided a method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5 to 10, by weight, based on the concentration of tocopherols, optionally in the presence of an acid catalyst, said by-product optionally containing additional $C_{10}$–$C_{22}$ fatty acids, at a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding said mixture to a first distillation zone comprising:
a first distillation apparatus selected from the group consisting of a short path evaporator, a wiped film evaporator, a centrifugal molecular still, and a falling film evaporator, operated at a temperature of about 170° C. to 270° C. and a pressure of about 0.05 to 10 torr,
wherein a vapor effluent comprised of a substantial fraction of the unreacted free fatty acids, and low-boiling materials is removed,
wherein a liquid effluent which is comprised of a tocotrienol/tocopherol-enriched mixture is removed;

(c) followed by feeding the liquid effluent from step (b) to a second distillation zone comprising:
a second distillation apparatus selected from the group consisting of a short path evaporator, a wiped film evaporator, a centrifugal molecular still, and a falling film evaporator, operated at a about 240° C. to 280° C. and a pressure of 0.01 to 2 torr,
wherein a vapor effluent comprised of remaining fatty acids and approximately 5 to 30 percent of total tocotrienols/tocopherols is removed, wherein a liquid effluent comprised of a tocotrienol/tocopherol-enriched mixture is removed; and (d) followed by feeding the liquid effluent from step (c) to a third distillation zone comprising:
a third distillation apparatus selected from the group consisting of a short path evaporator, a wiped film evaporator, a centrifugal molecular still, and a falling film evaporator, operated at a temperature of about 170° C. to 270° C. and a pressure of 0.005 to 2 torr, wherein a vapor effluent which is a tocopherol concentrate is removed and isolated.

It should be appreciated that the order of the fatty acid removal and high-boilers distillation may be reversed, i.e., steps (b) and (d) of the above aspects of the invention would be reversed. In this embodiment, the product of the esterification reactor (4) is fed first to distillation operation (11). The free fatty acids, low-boilers and tocotrienols/tocopherols are distilled overhead first from the sterol esters, fatty acid polyesters of glycerol, waxes, and other high-boiling compounds. The tocotrienol/tocopherol-rich distillate is then fed to distillation operation (5) to remove a substantial fraction of the fatty acids and low-boilers and then to distillation operation (8) to remove the remaining fatty acids and low-boilers. The final tocotrienol/tocopherol-rich concentrate is the bottoms product of distillation operation (8). The distillate of unit (8) may be recycled to the reactor (2), the first distillation (11), or the second distillation (5) in order to increase the overall tocotrienol/tocopherol recovery.

A more highly preferred embodiment of present invention is illustrated by FIG. 2. The vegetable oil by-product (1) is esterified in a batch or continuous reactor (2), with or without catalyst. The water of esterification is removed continuously via line (3) during the reaction. The product of the esterification step (4) is distilled under high vacuum to remove essentially all of the unreacted fatty acid, typically 90% to 99.9%, more typically 97% to 99.9%, along with a substantial fraction of other low-boilers via stream (8) to leave a tocotrienol/tocopherol-rich bottoms product (10). The temperature and pressure of the distillation is in the range of 220° C. to 320° C., 0.1 to 8 torr. The preferred range is 260° C. to 290° C., 0.5 torr to 4 torr. In the preferred embodiment of the invention, the distillation apparatus for the fatty acid removal step is a multistage, refluxed fractionating column. The column must contain at least one, preferably two to four, equilibrium stages of rectification (5), as well as an optional stripping section (6). The column must also have the capability of providing reflux via line (7) to the rectification section (5). The fractionating capability of the device greatly decreases the tocotrienol/tocopherol loss to the distillate to typically less than 5%, more typically 0.2% to 2.0%, and increases the removal of the free fatty acid from the bottoms product. The optional stripping section further increases the removal of the free fatty acids from the bottoms product. The extent of tocotrienol/tocopherol loss is highly dependent on the reflux ratio, defined as the ratio of the mass flow rate of stream (7) to the mass flow rate of stream (8). In the preferred embodiment of the invention the reflux ratio is in the range of 0.3 to 5.0, more preferably from 0.5 to 2.0. The staging in the rectification and optional stripping sections may be provided by any vapor-liquid contacting device, including bubble cap trays, sieve trays, random packing, and structured packing. In the preferred embodiment of the invention, the equilibrium staging is provided by high efficiency, low pressure drop structured packing, in order to lower residence time and reduce the temperature required for distillation. The reboiler of the distillation apparatus may be of any high-vacuum, low residence design including a short path evaporator, wiped-film evaporator, centrifugal molecular still, or falling film evaporator.

The tocotrienol/tocopherol-rich bottoms product (10) of the first distillation is then subjected to a second high-vacuum distillation (11). The tocotrienols/tocopherols and other similarly boiling compounds are collected as a tocotrienol/tocopherol-rich distillate product (12). The triglycerides, sterol esters, other high-boiling fatty acid esters, and other high-boiling compounds are removed in the largely tocotrienol/tocopherol-free bottoms, stream (13), of the distillation. Tocotrienol/tocopherol blend recovery to stream (12) is typically 95% to 100%, more typically 96% to 99.9%. The catalyst, if any were used, exits in the residue. The temperature and pressure of the second distillation is in the range of 170° C. to 300° C., 0.005 to 2 torr. The preferred range is 200° C. to 250° C., 0.01 torr to 0.05 torr. The distillation apparatus (11) may be of any high-vacuum design including a short path evaporator, wiped-film evaporator, centrifugal molecular still, or falling film evaporator.

Thus, as a further aspect of the present invention, there is provided a method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1, by weight, based on the concentration of tocopherols, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:

a first distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr, wherein a vapor effluent which is comprised of free fatty acids and low-boiling materials is removed; and wherein a liquid effluent which is comprised of a tocotrienol/tocopherol-enriched mixture is removed;

(c) followed by feeding the liquid effluent from step (b) to a second distillation zone comprising:

one or more separate distillation apparatus in series selected from the group consisting of a short path evaporator, a wiped film evaporator, a centrifugal molecular still, and a falling film evaporator, operated at a temperature of about 200° C. to 320° C. and a pressure of about 0.01 torr to 10 torr, wherein a liquid effluent comprised of sterol esters, fatty acid esters, glycerides, waxes, and other high-boiling materials is removed;

wherein a vapor effluent which is a tocotrienol/tocopherol blend concentrate is removed and isolated.

It should also be understood that the order of the fatty acid removal and high-boilers distillation may be reversed in this embodiment. In this embodiment, the product of the esterification reactor (4) is fed first to distillation operation (11). The free fatty acids, low-boilers, tocotrienols, and tocopherols are distilled overhead first from the sterol esters, fatty acid polyesters of glycerol, waxes, and other high-boiling compounds. The tocotrienol/tocopherol-rich distillate is then fed to a multi-staged fractionating distillation operation to remove essentially all of the fatty acids and a substantial fraction of the low-boilers. The distillation operation consists of a refluxed rectifying section (5), a reboiler (9), and an optional stripping section (6). The final tocotrienol/tocopherol-rich concentrate is the bottoms product of the second multi-staged distillation operation.

Accordingly, as a further aspect of the present invention, there is provided a method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1, by weight, based on the concentration of tocopherols, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:

one or more separate distillation apparati in series selected from the group consisting of a short path evaporator, a wiped film evaporator, a centrifugal molecular still, and a falling film evaporator, said apparati operated at a temperature of about 200° C. to 320° C. and a pressure of about 0.01 torr to 10 torr, wherein a liquid effluent comprised of sterol esters, fatty acid esters, glycerides, waxes, and other high-boiling materials is removed; and wherein a vapor effluent comprised of tocotrienols, tocopherols, free fatty acids and low-boilers is removed;

(c) followed by feeding the vapor effluent from step (b) to a second distillation zone comprising:

a distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr, wherein a vapor effluent which is comprised of free fatty acids, and low-boiling materials is removed;

wherein a liquid effluent which is a tocotrienol/tocopherol blend concentrate is removed and isolated.

EXPERIMENTAL SECTION

Example 1

A one liter 3-neck flask equipped with a mechanical stirrer, heating mantle, Dean-Stark trap, reflux condenser, nitrogen inlet, and thermowell was charged with 500 g of rice bran oil distillate comprised of tocols (2% tocotrienol and 1% tocopherol), sterols (1%), sterol esters (9%), free fatty acids (35%), hydrocarbons, and glycerides. The resulting mixture was stirred and heated for 7 hours at 200° C. A nitrogen flow of 100 mL/min was bubbled through the mixture during heating. The mixture was sampled and analyzed for tocols, sterols, sterol esters, fatty acids, and glycerides. The product mixture was distilled as described in Example 13 of U.S. Ser. No. 08/334,901. The distillate was composed mainly of fatty acids and squalene. The residue from the distillation was fed to a wiped film distillation apparatus as described in Example 14 of U.S. Ser. No. 08/334,901. The results of the distillations are listed in Table 1. Details of the utilization of other vegetable oil by-products can be found in our copending application, U.S. Ser. No. 08/334,901, incorporated herein by reference.

TABLE 1

Two-Step Distillation of Esterified Rice Bran Oil Distillate

| Reference No. | Stream | Mass (g) | Tocopherol Content (%) | Tocotrienol Content (%) | Sterol Content (%) | Sterol Ester Content (%) | Free Fatty Acid Content (%) |
|---|---|---|---|---|---|---|---|
| A | feed | 464 | 1.0 | 2.0 | 0.2 | 22.9 | 98.9 |
| B | distillate #1 | 89 | 0.0 | 0.0 | 0.0 | 0.0 | |
| | residue #1 | 374 | 0.7 | 0.8 | 0.2 | 25.5 | 2.1 |
| C | distillate #2 | 55 | 6.8 | 11.3 | 0.7 | 1.0 | 3.6 |
| | residue #2 | 305 | 0.1 | 0.0 | 0.1 | 32.8 | 5.6 |

We claim:

1. A method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1, by weight based on the concentration of tocopherols, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides; and (b) followed by subjecting said mixture to a series of distillation operations comprising:

(i) one or more separate distillation operations, wherein said distillation(s) is (are) conducted at a temperature of about 200° C. to 320° C. and a pressure of about 0.01 torr to 10 torr, in series wherein unreacted fatty acids and low-boiling components are removed as a vapor effluent and a liquid effluent comprised of tocotrienols/tocopherols is removed; and (ii) wherein said liquid effluent from step (b)(i) is subjected to one or more distillations in series, wherein said distillation(s) is (are) conducted at a temperature of about 170° C. to 270° C. and a pressure of about 0.005 torr to 2 torr, wherein a tocotrienol/tocopherol blend concentrate is removed as a vapor effluent and wherein a liquid effluent comprised of sterol esters, fatty acid esters, glycerides, waxes, and other high-boiling substances is removed.

2. The method of claim 1, wherein step (a) is conducted at a temperature of about 150° C. to 230° C. and a pressure of about 100 torr to 200 torr.

3. The method of claim 1, wherein additional $C_{10}$–$C_{22}$ fatty acids are added to the vegetable oil by-product utilized in step (a).

4. The method of claim 1, wherein an acid catalyst is utilized in step (a).

5. The method of claim 4, wherein the acid catalyst is selected from the group consisting of alkyl tin compounds, zinc salts of organic acids, zinc oxide, titanium (IV) alkoxides, and mineral acids.

6. A method for preparing a tocopherol/tocotrienol blend concentrate which comprises the steps:

(a) heating a vegetable oil by-product comprised of tocopherols, tocotrienols, fatty acids, sterols, sterol esters of fatty acids, and mono-, di-, and triglycerides, wherein said tocotrienols are present in a proportion of about 0.5:1 to 10:1 based on the concentration of tocopherols, said by-product optionally containing added $C_{10}$–$C_{22}$ fatty acids, optionally in the presence of an acid catalyst, at a temperature of about 70° to 300° C. and a pressure of about 50 torr to 760 torr, while continuously removing water formed thereby, to form a mixture comprised of sterol esters, high boiling fatty acid esters, waxes, and glycerides;

(b) followed by subjecting said mixture to distillation at a temperature of about 170° C. to 270° C. and a pressure of about 0.05 to 10 torr, while removing unreacted fatty acids and low-boiling components as a vapor effluent and a liquid effluent comprised of tocopherols and tocotrienols;

(c) followed by subjecting the liquid effluent from step (b) to distillation at a temperature of about 230° C. to 300° C. and a pressure of about 0.01 to 5 torr, while removing remaining fatty acids and approximately 5 to 30 percent of total tocopherols as a vapor effluent and a liquid effluent which is a tocopherol/tocotrienol-enriched product; and (d) followed by subjecting the liquid effluent from step (c) to distillation at a temperature of about 170° C. to 270° C. and a pressure of about 0.005 to 2 torr, and collection and isolation of a tocopherol/tocotrienol blend concentrate as a vapor effluent.

7. The method of claim 6, wherein step (a) is conducted at a temperature of about 200° C. to 240° C. and a pressure of about 0.5 to 4 torr; step (b) is conducted at a temperature of about 240° C. to 280° C. and a pressure of about 0.1 to 2 torr; step (c) is conducted at a temperature of about 200° C. to 240° C. and a pressure of about 0.01 to 0.05 torr; and step (d) is conducted at a temperature of about 260° C. to 290° C. and a pressure of about 0.5 to 4 torr.

8. The method of claim 6, further comprising the step of recycling the tocopherols removed as a vapor effluent in step (c) into the step (b) mixture.

9. The method of claim 6, wherein an acid catalyst is utilized in step (a).

10. A method for preparing a tocopherol/tocotrienol blend concentrate which comprises the steps:

(a) heating a vegetable oil by-product comprised of tocopherols, tocotrienols, fatty acids, sterols, sterol esters of fatty acids, and mono-, di-, and triglycerides, wherein said tocotrienols are present in a proportion of about 0.5:1 to 10:1 based on the concentration of tocopherols, said by-product optionally containing added $C_{10}$–$C_{22}$ fatty acids, optionally in the presence of an acid catalyst, to a temperature of about 70°–300° C. and a pressure of about 50 torr to 760 torr, to form a mixture comprised of sterol esters, high boiling fatty acid esters, waxes, and glycerides;

(b) followed by subjecting said mixture to distillation at a temperature of about 170° C. to 270° C. and a pressure of about 0.005 to 2 torr, while removing tocotrienols/tocopherols, free fatty acids, and low-boiling materials as a vapor effluent;

(c) followed by subjecting the vapor effluent of step (b) to distillation at a temperature of about 230° C. to 300° C. and a pressure of about 0.01 to 5 torr, thereby removing remaining fatty acids and approximately 5 to 30 percent of total tocopherols as a vapor effluent and a liquid effluent which is a tocotrienol/tocopherol enriched product; and (d) followed by subjecting the liquid effluent from step (c) to distillation at a temperature of about 170° C. to 270° C. and a pressure of about 0.05 to 10 torr, while removing unreacted fatty acids and low-boiling components as a vapor effluent and a liquid effluent which is a tocotrienol/tocopherol blend concentrate.

11. The method of claim 10, wherein step (a) is conducted at a temperature of about 200° C. to 240° C. and a pressure of about 0.5 to 4 torr; step (b) is conducted at a temperature of about 260° C. to 290° C. and a pressure of about 0.5 to 4 torr; step (c) is conducted at a temperature of about 200° C. to 240° C. and a pressure of about 0.01 to 0.05 torr; and step (d) is conducted at a temperature of about 240° C. to 280° C. and a pressure of about 0.1 to 2 torr.

12. The method of claim 10, further comprising the step of recycling the vapor effluent from step (c) into the step (b) mixture.

13. The method of claim 10, wherein an acid catalyst is utilized in step (a).

14. A method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1 based on the concentration of tocopherols, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:

a first distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr, wherein a vapor effluent which is comprised of free fatty acids and low-boiling materials is removed; and wherein a liquid effluent which is comprised of a tocotrienol/tocopherol-enriched mixture is removed;

(c) followed by feeding the liquid effluent from step (b) to a second distillation zone comprising:

one or more separate distillation apparatus in series selected from the group consisting of a short path evaporator, a wiped film evaporator, a centrifugal molecular still, and a falling film evaporator, operated at a temperature of about 200° C. to 320° C. and a pressure of about 0.01 torr to 10 torr, wherein a liquid effluent comprised of sterol esters, fatty acid esters, glycerides, waxes, and other high-boiling materials is removed;

wherein a vapor effluent which is a tocotrienol/tocopherol blend concentrate is removed and isolated.

15. The method of claim 14, wherein additional $C_{10}$–$C_{22}$ fatty acids are added to the vegetable oil by-product utilized in step (a).

16. The method of claim 14, wherein step (a) is conducted at a temperature of about 150° C. to 230° C. and a pressure of about 100 torr to 200 torr; step (b) is conducted at a temperature of about 260° C. to 290° C., a pressure of about 0.5 to 4 torr, and a reflux ratio of 0.5 to 2.0; and step (c) is conducted at a temperature of about 200° C. to 250° C. and a pressure of about 0.01 to 0.05 torr.

17. The method of claim 14, wherein an acid catalyst is utilized in step (a).

18. A method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1 based on the concentration of tocopherols, optionally in the presence of an acid catalyst, said by-product optionally containing additional $C_{10}$–$C_{22}$ fatty acids, to a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding the mixture from step (a) to a first distillation zone comprising:

one or more separate distillation apparatus in series selected from the group consisting of a short path evaporator, a wiped film evaporator, a centrifugal molecular still, and a falling film evaporator, said apparati operated at a temperature of about 200° C. to 320° C. and a pressure of about 0.01 torr to 10 torr, wherein a liquid effluent comprised of sterol esters, fatty acid esters, glycerides, waxes, and other high-boiling materials is removed; and wherein a vapor effluent comprised of tocopherols, tocotrienols, free fatty acids and low-boilers is removed;

(c) followed by feeding the vapor effluent from step (b) to a second distillation zone comprising:

a distillation apparatus comprised of a multistage, refluxed fractionating column and a reboiler, said column having a rectification section having at least one equilibrium stage of rectification and means for providing reflux to said rectification section, and optionally a stripping section, said apparatus operated at a temperature of about 220° C. to 320° C., and a pressure of about 0.1 to 8 torr, wherein a vapor effluent which is comprised of free fatty acids, and low-boiling materials is removed;

wherein a liquid effluent which is a tocotrienol/ tocopherol blend concentrate is removed and isolated.

19. The method of claim 18, wherein step (a) is conducted at a temperature of about 150° C. to 230° C. and a pressure of about 100 torr to 200 torr.

20. The method of claim 18, wherein additional $C_{10}$–$C_{22}$ fatty acids are added to the vegetable oil by-product utilized in step (a).

21. The method of claim 18, wherein step (b) is conducted at a temperature of about 200° C. to 250° C. and a pressure of about 0.01 to 0.05 torr.

22. The method of claim 18, wherein step (c) is conducted at a temperature of about 260° C. to 290° C., a pressure of about 0.5 to 4 torr, and a reflux ratio of about 0.5 to 2.0.

23. The method of claim 18, wherein step (a) is conducted at a temperature of about 150° C. to 230° C. and a pressure of about 100 torr to 200 torr; step (b) is conducted at a temperature of about 200° C. to 250° C. and a pressure of about 0.01 to 0.05 torr; and step (c) is conducted at a temperature of about 260° C. to 290° C., a pressure of about 0.5 to 4 torr, and a reflux ratio of about 0.5 to 2.0.

24. The method of claim 16, wherein an acid catalyst is utilized in step (a).

25. The method of claim 16, wherein the acid catalyst is selected from the group consisting of alkyl tin compounds, zinc salts of organic acids, zinc oxide, titanium (IV) alkoxides, and mineral acids.

26. The method of claim 16, wherein the acid catalyst is selected from the group consisting of butyl stannoic acid, zinc acetate, phosphoric acid, and dibutyl tin oxide.

27. A method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1 based on the concentration of tocopherols, optionally in the presence of an acid catalyst, said by-product optionally containing additional $C_{10}$–$C_{22}$ fatty acids, at a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding said mixture to a first distillation zone comprising:

a first distillation apparatus selected from the group consisting of a short path evaporator, a wiped film evaporator, a centrifugal molecular still, and a falling film evaporator, operated at a temperature of about 170° C. to 270° C. and a pressure of about 0.05 to 10 torr, wherein a vapor effluent comprised of a substantial fraction of the unreacted free fatty acids, and low-boiling materials is removed, wherein a liquid effluent which is comprised of a tocotrienol/tocopherol-enriched mixture is removed;

(c) followed by feeding the liquid effluent from step (b) to a second distillation zone comprising:

a second distillation apparatus selected from the group consisting of a short path evaporator, a wiped film evaporator, a centrifugal molecular still, and a falling film evaporator, operated at a about 240° C. to 280° C. and a pressure of 0.01 to 2 torr, wherein a vapor effluent comprised of remaining fatty acids and approximately 5 to 30 percent of total tocopherols is removed, wherein a liquid effluent comprised of a tocotrienol/ tocopherol-enriched mixture is removed; and (d) followed by feeding the liquid effluent from step (c) to a third distillation zone comprising:

a third distillation apparatus selected from the group consisting of a short path evaporator, a wiped film evaporator, a centrifugal molecular still, and a falling film evaporator, operated at a temperature of about 170° C. to 270° C. and a pressure of 0.005 to 2 torr, wherein a vapor effluent which is a tocotrienol/ tocopherol blend concentrate is removed and isolated.

28. The method of claim 27, wherein step (a) is conducted at a temperature of about 150° C. to 230° C. and a pressure of about 100 torr to 200 torr.

29. The method of claim 27, wherein additional $C_{10}$–$C_{22}$ fatty acids are added to the vegetable oil by-product utilized in step (a).

30. The method of claim 27, wherein step (b) is conducted at a temperature of about 200° C. to 240° C. and a pressure of about 0.5 to 4 torr.

31. The method of claim 27, wherein step (c) is conducted at a temperature of about 240° C. to 280° C. and a pressure of about 0.1 to 2 torr.

32. The method of claim 27, wherein step (d) is conducted at a temperature of about 200° C. to 240° C. and a pressure of about 0.01 to 0.05 torr.

33. The method of claim 27, wherein step (a) is conducted at a temperature of about 150° C. to 230° C. and a pressure of about 100 torr to 200 torr; step (b) is conducted at a temperature of about 200° C. to 240° C. and a pressure of about 0.5 to 4 torr; step (c) is conducted at a temperature of about 240° C. to 280° C. and a pressure of about 0.1 to 2 torr; and step (d) is conducted at a temperature of about 200° C. to 250° C. and a pressure of about 0.01 to 0.05 torr.

34. The method of claim 27, wherein tocopherols, tocotrienols and fatty acids removed as a vapor effluent in step (c) are recycled into the step (b) mixture.

35. The method of claim 27, wherein an acid catalyst is utilized in step (a).

36. The method of claim 27, wherein the acid catalyst is selected from the group consisting of alkyl tin compounds, zinc salts of organic acids, zinc oxide, titanium (IV) alkoxides and mineral acids.

37. The method of claim 36, wherein the acid catalyst is selected from the group consisting of butyl stannoic acid, zinc acetate, zinc oxide, phosphoric acid, titanium tetraisopropoxide and dibutyl tin oxide.

38. A method for preparing a tocotrienol/tocopherol blend concentrate which comprises the steps:

(a) heating a vegetable oil by-product comprised of tocopherols, tocotrienols, fatty acids, hydrocarbons, sterol esters of fatty acids, sterols, triterpenoid alcohols, methyl-sterols, and mono-, di-, and triglycerides, wherein said tocotrienols are present in a proportion of about 0.5:1 to 10:1 based on the concentration of tocopherols, optionally in the presence of an acid catalyst, said by-product optionally containing additional $C_{10}$–$C_{22}$ fatty acids, at a temperature of about 70° C. to 300° C. and a pressure of about 50 torr to 760 torr, while continuously removing water formed thereby, to provide a mixture comprised of sterol esters, high boiling fatty acid esters, waxes, and glycerides;

(b) followed by feeding said mixture to a first distillation zone comprising:
  a first distillation apparatus selected from the group consisting of a short path evaporator, a wiped film evaporator, a centrifugal molecular still, and a falling film evaporator, operated at a temperature of about 170° C. to 270° C. and a pressure of 0.005 to 2 torr,
  wherein a vapor effluent comprised of tocopherols, tocotrienols, unreacted free fatty acids, and low-boiling materials is removed,
(c) followed by feeding the vapor effluent from step (b) to a second distillation zone comprising:
  a second distillation apparatus selected from the group consisting of a short path evaporator, a wiped film evaporator, a centrifugal molecular still, and a falling film evaporator, operated at a temperature of about 170° C. to 270° C. and a pressure of about 0.05 to 10 torr,
  wherein a vapor effluent comprised of a substantial fraction of the unreacted free fatty acids, and low-boiling materials is removed, and
  wherein a liquid effluent which is a tocotrienol/tocopherol blend concentrate is removed and isolated; and
(d) followed by feeding the liquid effluent from step (c) to a third distillation zone comprising:
  a third distillation apparatus selected from the group consisting of a short path evaporator, a wiped film evaporator, a centrifugal molecular still, and a falling film evaporator, operated at a about 240° C. to 280° C. and a pressure of 0.01 to 2 torr,
  wherein a vapor effluent comprised of remaining fatty acids and approximately 5 to 30 percent of total tocopherols is removed,
  wherein a vapor effluent which is a tocotrienol/tocopherol blend concentrate is removed and isolated.

39. The method of claim 38, wherein step (a) is conducted at a temperature of about 150° C. to 230° C. and a pressure of about 100 torr to 200 torr.

40. The method of claim 38, wherein additional $C_{10}$–$C_{22}$ fatty acids are contacted with the vegetable oil by-product utilized in step (a).

41. The method of claim 38, wherein step (b) is conducted at a temperature of about 200° C. to 240° C. and a pressure of about 0.01 to 0.05 torr.

42. The method of claim 38, wherein step (c) is conducted at a temperature of about 200° C. to 240° C. and a pressure of about 0.5 to 4 torr.

43. The method of claim 38, wherein step (d) is conducted at a temperature of about 240° C. to 280° C. and a pressure of about 0.1 to 2 torr.

44. The method of claim 38, wherein step (a) is conducted at a temperature of about 150° C. to 230° C. and a pressure of about 100 torr to 200 torr; step (b) is conducted at a temperature of about 200° C. to 240° C. and a pressure of about 0.01 to 0.05; step (c) is conducted at a temperature of about 200° C. to 240° C. and a pressure of about 0.5 to 4 torr; and step (d) is conducted at a temperature of about 240° C. to 280° C. and a pressure of about 0.1 to 2 torr.

45. The method of claim 38, wherein tocopherols, tocotrienols, and fatty acids removed as a vapor effluent in step (d) are recycled into the step (b) mixture.

46. The method of claim 38, wherein tocopherols, tocotrienols and fatty acids removed as a vapor in step (d) are recycled into the step (c) mixture.

47. The method of claim 38, wherein an acid catalyst is utilized in step (a).

48. The method of claim 47, wherein the acid catalyst is selected from the group consisting of alkyl tin compounds, zinc salts of organic acids, titanias, and mineral acids.

49. The method of claim 47, wherein the acid catalyst is selected from the group consisting of butyl stannoic acid, zinc acetate, zinc oxide, phosphoric acid, and dibutyl tin oxide.

* * * * *